United States Patent [19]

Moest et al.

[11] Patent Number: 5,160,469
[45] Date of Patent: Nov. 3, 1992

[54] MANUFACTURE OF PELLETS OF XANTHINE DERIVATIVES

[75] Inventors: Thomas Moest; Claus H. Pich, both of Moorrege, Fed. Rep. of Germany

[73] Assignee: Nordmark Arzneimittel GmbH, Uetersen, Fed. Rep. of Germany

[21] Appl. No.: 578,442

[22] Filed: Sep. 7, 1990

[30] Foreign Application Priority Data

Sep. 8, 1989 [DE] Fed. Rep. of Germany ....... 3929864

[51] Int. Cl.$^5$ ............ B29B 9/08; A61K 9/16; A61K 31/52
[52] U.S. Cl. ................... 264/117; 424/469; 424/489; 424/490; 514/263
[58] Field of Search ............ 264/9, 15, 112, 117; 424/469, 489, 490; 514/263; 544/267, 273, 275

[56] References Cited

U.S. PATENT DOCUMENTS

| | | | |
|---|---|---|---|
| 3,864,469 | 2/1975 | Reiser et al. | 424/489 |
| 4,261,970 | 4/1981 | Ogawa et al. | 514/263 |
| 4,547,358 | 10/1985 | David et al. | 514/263 |
| 4,663,150 | 5/1987 | Panoz et al. | 424/494 |
| 4,670,438 | 6/1987 | Austel et al. | 514/249 |
| 4,692,337 | 9/1987 | Ukigaya et al. | 424/469 |
| 4,755,517 | 7/1988 | Bruns et al. | 514/263 |
| 4,786,509 | 11/1988 | Chang . | |
| 4,803,080 | 2/1989 | Benedikt et al. | 424/488 |
| 4,844,910 | 7/1989 | Leslie . | |
| 4,960,773 | 10/1990 | Korbonits et al. | 514/234.21 |
| 4,997,454 | 5/1991 | Violante et al. | 264/9 |

FOREIGN PATENT DOCUMENTS

| | | | |
|---|---|---|---|
| 1066029 | 11/1979 | Canada . | |
| 1178204 | 11/1984 | Canada | 424/490 |
| 3712058 | 10/1988 | Fed. Rep. of Germany . | |

*Primary Examiner*—Mary Lynn Theisen
*Attorney, Agent, or Firm*—Oblon, Spivak, McClelland, Maier & Neustadt

[57] ABSTRACT

A process for the manufacture of pellets which are composed of xanthine derivatives and are predominantly spherical, have a particle size in the range of 0.3 to 4 mm and have a bulk density above 0.5 g/cm$^3$ by reacting the appropriate xanthine derivative with water or a water/alcohol mixture, entails anhydrous powdered xanthine derivative with an average particle size of from 20 to 200 μm being suspended by stirring at from 40° to 70° C. in a nonsolvent which is immiscible with water and has a boiling point in the range from 60° to 160° C., then adding from 10 to 40% by weight, based on the anhydrous xanthine derivative, of water or a water/alcohol mixture and subsequently allowing to cool to room temperature at from 5° to 20° C. per hour, it being possible to reduce the stirring speed after agglomeration to about ⅓ to ⅔ of the original, and the pellets being separated from the liquid and dried, the pellets being used, possibly with a delayed release coating, as active compound in a drug.

4 Claims, No Drawings

MANUFACTURE OF PELLETS OF XANTHINE DERIVATIVES

The present invention relates to a straightforward process for the manufacture of pellets which are predominantly spherical and are 100% composed of xanthine derivatives and to the use thereof for the manufacture of delayed release drugs.

Conventional techniques for building up pellets require nonpareils as initial cores to be coated, or adhesives and/or other auxiliaries for producing a plastic composition.

These manufacturing processes are elaborate and they do not permit theophylline pellets with the maximum, ie. 100%, concentration of active compound to be manufactured, and thus the density of active compound is limited. However, a high density of active compound is necessary to be able to pack larger quantities of drug into hard gelatin capsules of acceptable size.

Pure theophylline agglomerates have likewise been disclosed and can be obtained either by disintegrating granulation of compacted theophylline or, as stated in DE-A 3,712,058, by forcing theophylline/water mixtures through perforated plates to give extrudates. The person skilled in the art is aware that these pellets do not have the desired spherical shape for achieving good flow properties and maximum bulk density. Although DE-A 3,712,058 mentions further processing to round pellets, an additional step is necessary for this, so that the result would be three stages in the shaping process: mixing - extrusion - final shaping. Apart from this, it is unclear how this final shaping to round pellets is to be carried out because, according to the statements in DE-A 3,712,058, the moist theophylline composition tends to solidify very rapidly.

Hence it was an object of the present invention to manufacture in a straightforward manner pellets which are as nearly spherical as possible, are composed of xanthine derivatives in a concentration of 100% and, at the same time, have a bulk density exceeding 0.5 g/cm$^3$ and thus permit a high density of active compound, eg. in capsules.

We have found that this object is achieved by a process for the manufacture of pellets which are composed of xanthine derivatives and are predominantly spherical, have a particle size in the range from 0.3 to 4 mm and have a bulk density above 0.5 g/cm$^3$ by reacting xanthine derivatives with water or water/alcohol mixtures, entailing powdered xanthine derivative with an average particle size of from 20 to 200 μm being suspended by stirring at from 40° to 70° C. in a nonsolvent which is immiscible with water or water/alcohol mixtures and has a boiling point in the range from 60° to 160° C., then adding from 10 to 40% by weight, based on the xanthine derivative, of water or water/alcohol mixtures and subsequently allowing to cool to room temperature at from 5° to 20° C. per hour, it being possible to reduce the stirring speed after agglomeration to about ⅓ to ⅔ of the original, and the pellets being separated from the liquid and dried.

In another aspect of this invention, we have found a drug for oral use which contains as active compound per dose from 100 to 600 mg of pellets or delayed release pellets of xanthine derivative manufactured according to the above described process.

Xanthine derivatives within the meaning of the present invention are 2,6-dihydroxypurines which are N-substituted two or three times, preferably caffeine, pentoxifylline, diprophylline, etofylline, doxofylline and, in particular, theophylline.

The water/alcohol mixtures contain a maximum of 50, preferably 20 or less, percent alcohol.

The powder is dispersed in the nonsolvent while stirring continuously at an incipiently turbulent rate, it being immaterial whether the powder or the nonsolvent is introduced first. No emulsifier is necessary. The nonsolvent can be heated to from 40 to 70, preferably 40° to 50° C. before or after the powder is suspended in it. After the water or water/alcohol mixture has been added, which can take place slowly or quickly, dropwise or all at once, the temperature is allowed to fall at from 5 to 20, preferably about 10° C. per hour, it being possible to reduce the stirring speed to about ⅔ to ⅓ of the original when the initially cloudy dispersion of the powder has become clear due to agglomeration. The average particle size of the pellets can be adjusted in the range from 0.3 to 4, preferably 0.8 to 2, mm depending on the particle size of the powdered xanthine derivative, the amount of water or water/alchol mixture added and the stirrer speed. The particle size distribution is usually narrow within this range, and the particles are uniformly spherical. After cooling to room temperature, they are separated from the liquid and dried in a conventional manner (cf. textbooks on pharmaceutical technology) at from 60° to 80° C. Their bulk density is above 0.5, preferably above 0.6, g/cm$^3$. They are non-friable and their hardness is high. In an apparatus for determining the friability (Born Friabimat SA 400, from Born Gerätebau, D 3554 Gladenbach) the friability found after the very extreme test of shaking at 999 min$^{-1}$ for 180 sec was only 0.8% or below.

The ratios of the amounts of xanthine derivative to nonsolvent which is immiscible with water or water/alcohol mixtures and to water or water/alcohol mixture are in the range 1 kg: 1 to 4 1 : 0.2 to 0.4 1.

Particularly suitable nonsolvents which are immiscible with water or water/alcohol mixtures and boil in the range from 60 to 160, preferably 70° to 130° C., are medium chain-length alkanes such as cyclohexane or petroleum ethers. A "nonsolvent which is immiscible with water or water/alcohol mixtures" is defined as a liquid which dissolves negligible amounts of xanthine derivative or water or water/alcohol mixtures, in other words two phases are always formed on mixing any two of the three components in the ratios indicated above.

The "average particle size" means the weight average.

"Predominantly spherical" pellets means that the diameters of a pellet at right-angles to one another do not differ by more than 25, preferably not more than 15%.

The pellets can be packed in hard gelatin capsules or in dosed wafers with or without providing a release-delaying (and/or enteric) coating. Release-delaying coatings contain the diffusion-controlling polymers which are customary for this purpose, are insoluble in aqueous medium irrespective of the pH and are described in textbooks and handbooks of pharmacy, for example poly(meth)acrylates, cellulose derivatives and vinyl polymers. Owing to the high mechanical strength, the predominantly spherical shape and the uniform surface of the pellets, it is possible to obtain a controlled release of active compound in a straightforward manner with very small amounts of coating in any suitable coater. The uniformly spherical pellets can be used for precise, high-density packing of capsules, resulting in capsules with a high content of active compound.

By drug forms which contain the pellets manufactured according to the invention are meant hard gelatin capsules, dosed wafers and tablets which have been compressed from the pellets using binders and possibly other conventional pharmaceutical auxiliaries.

EXAMPLE 1

2 l of petroleum ether boiling in the range from 100° to 130° C. were heated while stirring to 45° C. in a 3 l jacketed vessel with propeller agitator and baffles. 1 kg of powdered theophylline of average particle size 100 μm was suspended in this at a circumferential speed of 5.4 m/s. 0.3 l of water was stirred into this suspension. The circumferential speed was reduced to 3.4 m/s after agglomeration of the suspended particles, the mixture was slowly cooled at about 10° C./h to about 20° C., and then the pellets were removed by filtration with suction and were dried in a suitable explosion-protected oven at about 60° C.

The particle size of the pellets ranged from 500 to 1800 μm, with a pronounced maximum at 900 μm.

The bulk density determined by the DIN 53,468 method was 0.62 g/cm$^3$. The friability determined with a 100 μm screen after 15 min in a dry fluidized bed was below 0.2%.

EXAMPLE 2

600 ml of petroleum ether boiling in the range from 100° to 130° C. were heated while stirring to 60° C. in a 1 l jacketed vessel with inclined blade agitator and baffles. 200 g of powdered pentoxifylline with particles ranging up to 200 μm were suspended in this at a circumferential speed of 1.7 m/s.

30 ml of a water/ethanol mixture were stirred into the suspension. After cooling at about 10° C./h to 20° C., the resulting pellets were filtered off with suction and dried in a suitable explosion-protected oven at about 60° C.

The particle size of the pellets ranged from 400 to 1300 μm with a maximum at 800 μm.

The bulk density determined by the DIN 53,468 method was 0.64 g/cm$^3$.

The friability determined with a 100 μm screen after 15 min in a dry fluidized bed was less than 0.3%.

We claim:

1. A process for the manufacture of pellets which are composed of xanthine derivative and are predominantly spherical, have a particle size in the range from 0.3 to 4 mm and have a bulk density of above 0.5 g/cm$^3$ by reacting xanthine derivatives with water or water/alcohol mixtures, comprising suspending a powdered xanthine derivative with an average particle size of 20 to 200 μm by stirring at from 40° to 70° C. in a nonsolvent which is immiscible with water and has a boiling point in the range from 60° to 160° C., allowing the xanthine derivative to agglomerate into pellets by adding from 10 to 40% by weight, based on the xanthine derivative, of water or a water/alcohol mixture and subsequently allowing to cool to room temperature at from 5° to 20° C. per hour, and separating the pellets from the liquid and drying.

2. The process according to claim 1 comprising a further process step of reducing the stirring speed after agglomeration to about ⅓ to ⅔ of the original stirring speed.

3. A process for the manufacture of delayed release pellets which are composed of xanthine derivative and are predominantly spherical, have a particle size in the range of 0.3 to 4 mm and have a bulk density above 0.5 g/cm$^3$ by reacting xanthine derivatives with water or water/alcohol mixtures, comprising suspending a powdered xanthine derivative with an average particle size of 20 to 200 μm by stirring at from 40° to 70° C. in a nonsolvent which is immiscible with water and has a boiling point in the range of from 60° to 160° C., allowing the xanthine derivative to agglomerate into pellets by adding from 10 to 40% by weight, based on the xanthine derivative, of water or a water/alcohol mixture and subsequently allowing to cool to room temperature at from 5° to 20° C. per hour, separating the pellets from the liquid and drying, and coating the pellets with at least one diffusion-controlling polymer which is insoluble in aqueous medium.

4. The process according to claim 3, comprising a further process step of reducing the stirring speed after agglomeration to about ⅓ to ⅔ of the original stirring speed.

* * * * *